(12) United States Patent
Paley

(10) Patent No.: US 6,221,662 B1
(45) Date of Patent: Apr. 24, 2001

(54) TRYPTAMINE TREATED, HUMAN DIFFERENTIATED, NEURONAL ALZHEIMER-LIKE CELL AND ATTENDANT METHODS OF CELL MODELING

(76) Inventor: Elena Paley, 9257 Emerson Ave., Surfside, FL (US) 33154

( * ) Notice: Subject to any disclaimer, the term of this patent is extended or adjusted under 35 U.S.C. 154(b) by 0 days.

(21) Appl. No.: 09/384,869

(22) Filed: Aug. 27, 1999

(51) Int. Cl.[7] ...................................................... C12N 5/08

(52) U.S. Cl. .......................... 435/368; 435/325; 435/377; 435/383; 435/441

(58) Field of Search .................................... 435/368, 377, 435/325, 383–385, 441

(56) References Cited

PUBLICATIONS

De Boni, U, Prog. Clin. Biol. Res, 253:33–43, 1987.*
Ross et al, Cancer Research, Oct. 1, 1983 71(4):741–7.*
Ko Li–wen ert al, Brain Research, 707(2): 256–65, 1996.*
Sadee et al, Cancer Research, Oct. 1, 1987 47: 5207–212.*
Sato et al, In Basic Cell Culture, A Practical Approach, Chapter 6, p 108, EDT.JM Davis, Oxford University Press, 1994.*
Crimo et al, Brain Research, Dec. 18, 1989 504(2): 247–57.*
Van Den Eijnden–Van Raaij, A. J. M., et al, Experimental Cell Research, 178(2): 479–792, 1988.*

* cited by examiner

Primary Examiner—Jeffrey Stucker
Assistant Examiner—Ulrike Winkler
(74) Attorney, Agent, or Firm—McDermott, Will & Emery

(57) ABSTRACT

A cellular model and attendant methodology wherein the cellular model expresses Alzheimer-like lesions or characteristics resulting from the consequences of the natural inhibitory effects of tryptamine on enzyme activity of aminoacyl-tRNA synthetase in human differentiated neuronal cells. Epithelial cells are segregated from neuroblast cells in a human neuroblast cell line, by either subjecting the neuroblast cell line to the inhibitory effects of tryptamine or alternately removing the neuroblast cells from the epithelial cells by utilization of a washing solution of trypsin. The methodology for generation of the cellular models results in a plurality of distinct cell groupings each of which may be used for control cellular models or for analyses purposes, wherein the plurality of groupings of epithelial cells comprise a first grouping expressing differentiated neuron-axon phenotype, a second grouping characterized by the epithelial cells being untreated and unaffected by the inhibitory affects of tryptamine, and a third grouping characterized by an acute treatment with tryptamine subsequent to separation from the neuroblast cells. The effectiveness of the cellular model producing methodology is evaluated based on immunogold electron, immunofluorescent and immunoperoxidase light microscopic identification of the Alzheimer's-like indicators including intra-and extracellular neurofibrillary tangles in the differentiated neuronal human cells and extracellular plaques.

9 Claims, 2 Drawing Sheets

TRYPTAMINE TREATED, HUMAN DIFFERENTIATED, NEURONAL ALZHEIMER-LIKE CELL AND ATTENDANT METHODS OF CELL MODELING

BACKGROUND OF THE INVENTION

1. Field of the Invention

This invention relates to the development of tryptamine-induced cellular models expressing Alzheimer like lesions resulting from the consequences of the natural inhibitory effect of tryptamine on aminoacyl-tRNA synthetase enzyme activity in human differentiated neuronal cells, as well as the development of a diagnostic test for the detection of Alzheimer's disease, based upon novel biological markers involved in aberrant cell signal transduction. The effectiveness of the model producing treatment is evaluated based on fluorescent, light and immunogold electronic microscopic identification of the Alzheimer-like immunoimorphological indicators, including neurofibrillary tangles and extracellular plaques attached to cells or substrate in tryptamine treated differentiated neuronal human cells and the search for aminoacyl-tRNA synthetase.

2. Description of the Related Art

Alzheimer's disease affects an estimated 4 million people throughout the United States alone and is characterized by progressively worsening memory loss and eventual dementia. Currently, 1 in 10 people over the age of 65 suffer from some stage of the disease. In addition, half of all people over the age of 85 demonstrate some symptomatic signs of Alzheimer's disease. Currently, the definitive diagnosis for Alzheimer's disease can only be made after a patient's death, when the autopsied brain tissues can be studied. Absent that, doctors and medical researchers look for evidence of memory and thinking difficulties, symptoms that show themselves only once the disease has advanced. Other recognized tools for the determination of the existence of Alzheimer's disease include CAT scans and magnetic residence imaging (MRI). Both of these techniques only show damage to the brain cells once the Alzheimer's disease is taken a firm hold. Family history is also recognized as an important clue to the likely presence of such a disease.

Extensive study and research throughout the world are currently being conducted on a variety of different levels in order to find a cure and/or a preventative treatment for the Alzheimer's disease. Recent studies published in the British journal NATURE reported the possibility that Alzheimer's disease could one day be treated or even prevented through the injection of a relatively simple vaccine. Typically, people suffering from Alzheimer's disease have abnormal deposits of extracellular plaques in their brain. Such plaques are formed of a protein substance called beta amyloid. Certain researches believe that people's immune systems eventually could be harnessed to fight off such plaque deposits. The aforementioned study involves the injection of a synthetic form of beta amyloid into mice that are genetically engineered to quickly develop Alzheimer-like plaques. Continuous research indicated that after a period of approximately one year the injected mice had developed antibodies against the brain clogging proteins and that the antibodies had triggered an immune response. After dissection, the autopsied brain cells of immunized mice indicated that 7 out 9 had no detectable plaque deposits in their brain. In addition, older mice, which already suffered from plaque build up received the synthetic beta amyloid injections resulting in the immune systems of the older mice attacking and destroying the previously existing plaque.

In spite of the advancements in the research, of the type set forth above, scientist are still in disagreement about whether beta amyloid proteins are the cause of Alzheimer's disease or simply a symptom of the disease. Beta amyloid is a part of larger molecule, Beta-amyloid precursor protein, that is normally an essential part of human cell membranes. In more simplistic terms, enzymes cut off small pieces of the protein, leaving them to circulate in the blood stream. In healthy people not afflicted with Alzheimer's disease, the protein particles readily circulate and do not seem to cause a problem. However, in those afflicted with Alzheimer's disease, the protein particles attach themselves to neurons and extracellular plaques are formed. At this point in Alzheimer's disease research, scientists still do not know the cause of the protein attachment to the neuron.

While studies of the type set forth above are encouraging and at least have the effect of directing or focusing further research efforts on discovery of a preventative or cure for Alzheimer's disease, it is readily recognized by experts in the field, that plaque causing protein in mice are different from those found in humans. It is also obvious that the immune system and general physiological make-up of mice are distinct from humans. However, perhaps the most apparent distinction is the unavailability of any cell model originating from animals, which demonstrate neurofibrillary tangles, wherein affected human cells demonstrate both senile plaque and neurofilament tangles. Accordingly, in order to properly research the cause is and/or factors and possible treatments associated with Alzheimer's disease, a complete investigation and research should be developed which involve the intracellular tangles of paired helical or straight neurofilaments as well as that of extra cellular senile plaques.

Regardless of the specific focus or direction researchers take, it is obvious that there is an urgent need in the medical field for new advancements in research techniques and procedures, which, while not necessarily accomplishing a cure or preventative for the disease, will greatly enhance the direction and focus of research in numerous areas of Alzheimer's disease. Such a technical advancement would preferably be in the form of a "cellular model" which closely resembles or effectively duplicates an Alzheimer's cell and which would be readily available to researchers and thereby lessen the reliance on the study of affected animal brain tissue or autopsied brain cells from humans.

SUMMARY OF THE INVENTION

Alzheimer's disease is an age related neurodegenerated disease of unknown origin, mainly characterized by the detectable presence of intracellular tangles of paired helical or straight neurofilaments with a diameter of 8–20 nm and extracellular senile plaques. The degenerating process and the resulting neuronal loss leads to memory impairment and to subsequent dementia. Drugs, as a course of treatment to combat Alzheimer's disease, are urgently needed. Studies of the prevention and treatment of patients with existing Alzheimer's symptoms are complicated by the fact that a reliable diagnosis currently depends on post-mortem analyses of brain tissue. Animal and/or cellular models which would facilitate investigation of an eventual cure and treatment of Alzheimer's disease, and which in particular address the characteristics of intracellular tangles are not yet available.

The substance tryptamine is a biogenic amine, decarboxileated analog of tryptophan and is a common and varied constituent found in a variety of foods. Tryptamine is characterized by the fact that once consumed, it can easily cross the blood-brain barrier. Accordingly the present invention recognizes that providing a tryptamine-induced cellular model expressing Alzheimer's infected characteristics would be a physiologically relevant tool to the investigation of the cause and treatment of Alzheimer's disease.

Looking specifically to the present invention, a human cultured neuroblast cell line is utilized in the procedures comprising the development of the cellular model of the present invention as set forth in greater detail hereinafter. One specific human neuroblast cell line which may be utilized is (SHSY5Y) and was established by Biedler et al. However, this cell line is representative only of other human cell lines that may be utilized. Moreover, the cell line utilized preferably includes identifiable quantities of epithelial cells, which are predominant for the identification of modeled cells in the present invention. In particular, the methods for creating the preferred cellular models of the present invention involve the selection of epithelial cells since such cells will optimally exhibit the Alzheimer's characteristics for analysis.

With the appropriate human neuroblast cell line specimen selected, the epithelial cells, either in a natural state within the cell line, defined as being co-mingled with neuroblast cells, or in an isolated state, defined as being segregated from the neuroblast cells, are treated with a quantity of tryptamine for a predetermined period of time and subsequently cultivated. In the case of the co-mingled epithelial cells, the tryptamine exposure results in the treated epithelial cells expressing a differentiated neuron-axon phenotype. The affected epithelial cells can then be generally defined as a first grouping of epithelial cells and can be isolated for proper study and analysis, including comparison to one or more control samples. One such control sample to which the affected epithelial cells can be compared for identification of the characteristic tangles and plaques, is cellular tissue from a human cadaver, known to be infected with Alzheimer's disease.

In addition to the above, however, a secondary cell model specimen is preferably generated. This secondary cell model is generated for purposes of generating a second grouping of epithelial cells, distinguishable from the first grouping by isolating epithelial cells which have not been treated with the tryptamine. More specifically, a separation method devoid of exposure of the epithelial cells to the inhibitory effects of tryptamine, is utilized. This secondary method preferably comprises the washing out of the neuroblast cells with a trypsin solution, thereby segregating the epithelial cells. Once isolated, some of the isolated epithelial cells can be used as a secondary or base line control cells. In addition, a segregated portion of the neuronal cells, treated as set forth above, to isolate the epithelial cells without initial tryptamine exposure, are subsequently acutely treated with tryptamine for a predetermined period in a culture medium along with other predetermined supplements. Specifically, the acute treatment of the isolated epithelial cells more effectively ensures the isolation of model cells containing the characteristic neurofibrillary tangles along with extracellular plaques in the epithelial cells. However, such a modeling may be viewed as secondary, as the tryptamine treatment takes place in a more concentrated manner outside of the traditional human neuroblast cell line.

As a result of the above, three distinct cell groupings or cellular control groups are preferably defined by the methods of the present invention and maintained in a buffer solution for analysis purposes. More specifically, the following three cellular control groups are produced and can be used for routine immunomorphological analysis under fluorescent, light and electron microscopy:

a) epithelial cells expressing differentiated neuron-axon phenotype;

b) untreated epithelial cells c) acute tryptamine-treated cells.

With the preceding groupings defined, commercial monoclonal or polyclonal antibodies to tau-protein, Beta-amyloid, neuronal markers, congo red staining and hematoxylin counterstaining are then used for the identification of the Alzheimer's lesions. Autopsied brain sections of Alzheimer's, as well as non-Alzheimer's patients and mice are also preferably processed for routine, light and polarized light microscopic immunohistological analyses in controlled comparison with the produced cellular models.

BRIEF DESCRIPTION OF THE DRAWINGS

For a fuller understanding of the nature of the present invention, reference should be had to the following detailed description taken in connection with the accompanying drawing in which.

DETAILED DESCRIPTION OF THE PREFERRED EMBODIMENT

Figure 1:
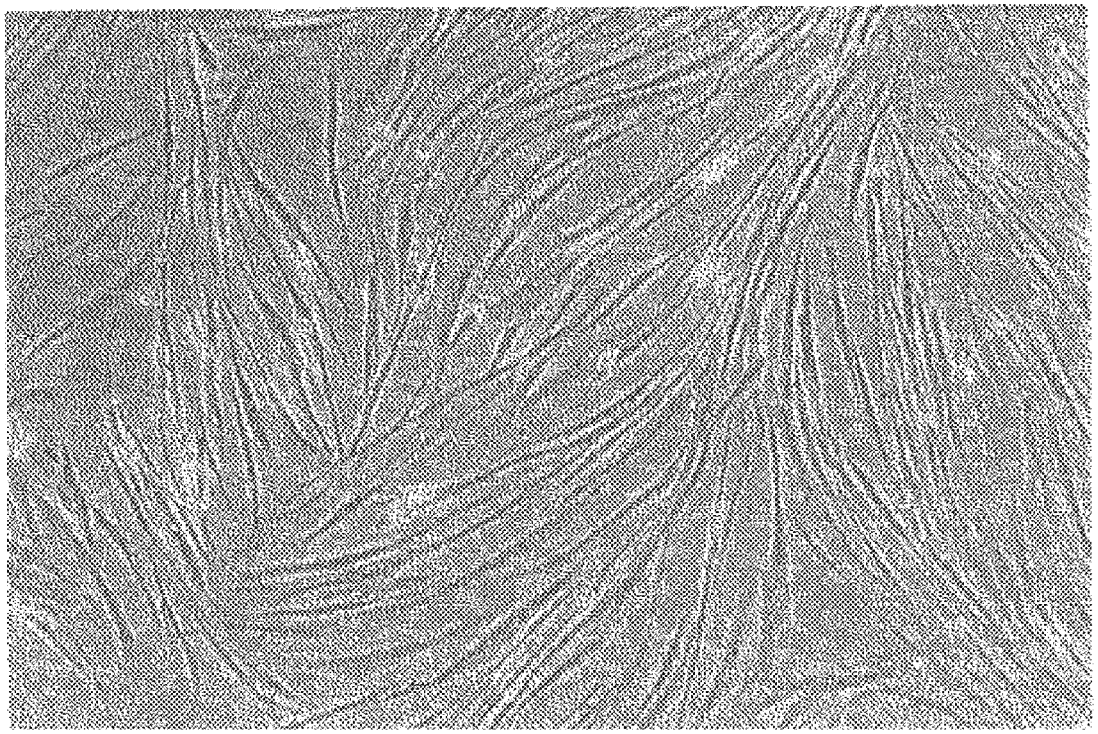
FIG. 1 illustrates a population of epithelial cells demonstrating different degrees of neuron-axon development subsequent to predetermined exposure to tryptamine.

The present invention is directed towards the generation and utilization of cellular models for the purpose of modeling Alzheimer's characteristics in human brain tissue.

In one embodiment of the present invention, a human neuroblast cell line, such as but not limited to, the human neuroblast cell line (SHSY5Y) as established by Biedler et al., is selected and initially cultivated for use. A primary characteristic for the preferred selection and usage of a human cell line relates to its inclusion of identifiable quantities of epithelial cells. In the embodiment referred to, the selected cell line generally comprises approximately 97% neuroblast cells and approximately 3% epithelial cells. It is preferably with the epithelial cells that the primary modeling takes place. As a result, the preferred methods of the present invention preferably involve the segregation, cultivation and isolation of epithelial like cells.

In a first embodiment of the present invention, the epithelial cells are treated in their cell line state along with the neuroblastic cells. Specifically, the cell line is treated with generally between 20 to 40 micrograms/milliliter of tryptamine for a period of between 6 to 8 weeks, including 5 to 6 passages. The result of this exposure to tryptamine demonstrates, subsequent to the indicated period of treatment, the deferential killing of the neuroblastic cells. The surviving epithelial cells are then cultivated for a period of several months without exposure to the inhibitory effects of tryptamine. This allows the full effects of the inhibitory effects of the treatments to be exhausted. At this point the pretreated epithelial cells are preferably isolated for analysis as control cells and may be generally defined as a first grouping of cells for use as a control group.

In this first embodiment of the present method, the epithelial cells were segregated, based upon certain characteristics exhibited by the epithelial cells versus the neuroblast cells. Specifically, the epithelial cells were segregated, at least in part, based upon the differential inhibitory effect of tryptamine on neuroblast cells as versus epithelial cells.

For example, the neuroblast cells are generally significantly more sensitive to the inhibitory effects of tryptamine at least partially based upon the existence of different adhesive properties of the epithelial cell and the neuroblast cell populations, wherein epithelial cells demonstrate stronger adherence properties.

Once the separation of the epithelial cells is achieved based on the inhibitory effects of the exposure to tryptamine, the epithelial cells express a differentiated neuron-axon phenotype. Indeed, this characteristic has led to the following conclusions, namely:

1. The aforementioned tryptamine treatment led to the differentiation of neuronal cells as well axon growth.
2. Tryptamine neurodegenerative effect can be reversed.
3. Tryptamine can easily eliminate the highly malignant neuroblastic cells at least following 5 to 6 passages.

From the epithelial cells remaining, a selection process must then take place in order to identify the optimal epithelial cells for modeling purposes. Specifically, based at least in part on the cell line treatment environment, not all of the epithelial cells will exhibit the same degree of reactivity to the treatment. Accordingly, as shown in FIG. 1, a population of epithelial cells is represented which clearly exhibit different degrees of differentiation or neuron-axon development. Further, FIG. 1 represents phase contrast light microscopy of living differentiated neuronal cells. Preferably, the epithelial cells which demonstrate optimal characteristics for modeling include those epithelial cells which demonstrate advanced neuron-axon development, without complete conversion. Only approximately 3% of the neuroblastic cell line comprises the epithelial cells, and from those, only a portion exhibit the optimal characteristics and/or neuron-axon development, as demonstrated in FIG. 1. This is a primary reason for the generation of the third control grouping to be described, however, the ultimately derived cellular models achieved to define the first control grouping are still ultimately preferred. Furthermore, the actual selection of the optimal cellular models for the first control grouping is preferably achieved through a visual analysis and differentiation of all of the treated epithelial cells present.

In addition to the above methodology for the formation and isolation of a cellular model of the present invention, it is also preferred that a second control grouping of untreated epithelial cells be generated. Therefore, at least some of the neuronal cells are also preferably treated in media lacking the tryptamine inhibitor, and are more specifically defined by a cell population enriched in epithelial cells, selected without the utilization of tryptamine or other inhibitor agents. As the above described selection characteristics are not available for monitoring with the sample being treated with tryptamine, the selection in this phase is preferably accomplished by washing out the neuroblast cells with a trypsin solution. The result is an isolated population of epithelial cells, untreated with tryptamine, and which may generally be defined as a second grouping of cells, at least some of which can be used as either a secondary or base control group for comparison purposes.

Figure 2:
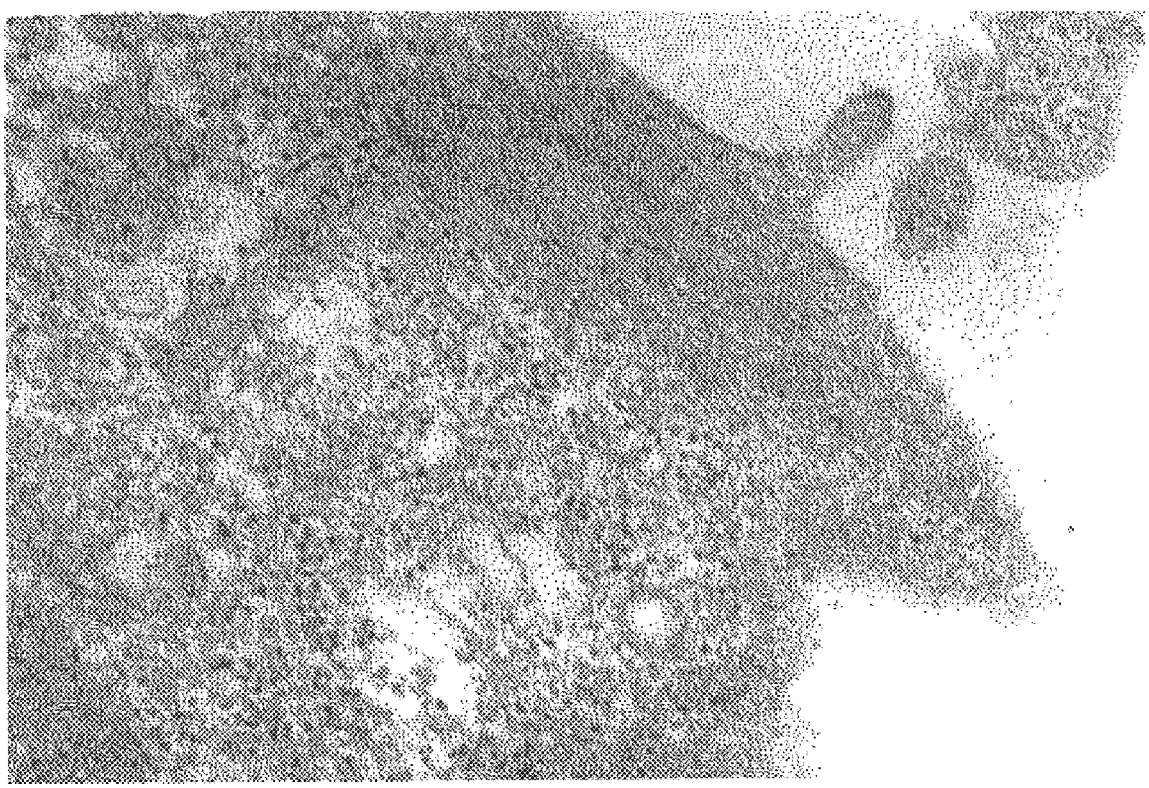
FIG. 2 illustrates an epithelial cell demonstrating new neurofibrillary tangles observed by means of immunogold or morphological electron microscopy.

In addition to the utilization of the untreated, isolated epithelial cells as a control group, at least a portion of the epithelial cells, being initially untreated, are preferably utilized for a more focused or acute tryptamine treatment phase, thereby providing a further, more concentrated specimen for analysis and/or comparison. In particular and as shown in FIG. 2, a third grouping of epithelial cells may be generated by separating out a portion of the untreated second grouping of cells, isolated in the manner as set forth above. The separated third grouping of cells are then acutely treated utilizing generally about 50–100 micrograms/milliliter of tryptamine. More specifically, FIG. 2 represents the third grouping of epithelial cells using immunogold morphological electron microscopy analysis following substantially six days of treatment in an RPMI 1640 cultural medium resulting in the demonstration of new neurofibrillary tangles. A more prolonged treatment of up to substantially sixty days may be used to examine changes of cytoskeleton associated tryptophanyl-tRNA synthetase (TrpRS) protein in imunochemical analysis. Supplements, added to the cultural medium, included 10% fetal calf serum as well as predetermined antibiotics.

As a result of the above indicated methodology, three distinct cell groupings were defined for use as control cells analysis purposes. More specifically, the following three cellular control groups were used for routine immunomorphological analysis under light and electron microscopy:

a) a first grouping of epithelial like cells; expressing differentiated neuron-axon phenotype;

b) a second grouping of untreated epithelial cells;

c) a third grouping of acute tryptamine-treated cells.

All of the above three grouping of control cells are preferably fixed in a PBS buffer solution containing substantially 4% formaldehyde and substantially 0.25% glutaraldehyde for a period of 30 minutes at room temperature. Additionally a human cadaver cell tissue model is also preferably utilized as a further control to identify the modeled cells exhibiting the Alzheimer's characteristics.

In order to identify the affected cell models, two distinct monoclonal antibodies, IgG1 class 6C10/C9 and 9D7, raised to bovine TrpRS and anti-bovine TrpRS polyclonal antibodies retrieved from a plurality of different immunized rabbits, are also preferably used for the first time for immunochemical analysis of the human neuronal cells and autopsied brain section. Specificity of the antibodies were verified with biochemically isolated bovine TrpRS (Fractogel fraction), and recombinant human TrpRS expressing in *E. coli*.

Furthermore, commercial monoclonal or polyclonal antibodies to tau-protein, Beta-amyloid, and neuronal markers are also to be used for the identification of the Alzheimer's lesions. Autopsied brain sections of Alzheimer's, as well as non-Alzheimer's patients and mice were processed for routine light and polarized light microscopic immunohistological analysis in controlled comparison with the produced cellular models.

From the preceding, properly affected and useable cellular models can be generated based primarily on the use and recognition of the possibility of using TrpRS and its inhibitor, tryptamine in the creation of tryptamine-induced cellular models expressing Alzheimer's type lesions and addressing the tangle characteristic of an Alzheimer affected cell. Naturally, these cellular models appear to be a physiologically relevant tool for further pursuing the diagnosis, prevention and treatment of Alzheimer's disease. Areas to be pursued are varied and extensive and include, by way of example:

1) The development of new human and animal cellular models treated with biogenic amines, analogs of the other amino acids (such as histamine, tyramine, etc.); potential amyloidogenic residue motives, stretches of amino acids, which are commonly found in amyloidogenic proteins, were also found in most if not all known 20 human AaRS.

2) Potential transgenic animal models would be represented by a chromosome 14 locus related to some familial cases of Alzheimer's disease would be established. Human TrpRS localization on the same region of chromozone 14 is confirmed. When genetic loci of TrpRS in familial cases of Alzheimer's; disease are characterized, transgenic manipulation will be undertaken. These transgenic manipulations for genetic lesions will be introduced in mice.

3) Potential treatment strategies could also involve pharmacological screening of effective tryptamine brain receptor antagonists for anti-Alzheimer's drug development using cellular and animal models.

4) Development of diagnostic tests for Alzheimer's disease based on the discovery of TrpRS in extracellular plaques: the screening of secreted TrpRS forms in human fluids using monoclonal and polyclonal antibodies to TrpRS.

5) The development of diagnostic test for Alzheimer's disease based on the tryptamine induction of Alzheimer's lesions in cells resulting in the measurement of tryptamine and its metabolites levels in human fluids.

6) Potential prevention strategies towards Alzheimer's disease may include:
   a) measurement of tryptamine levels in various food products;
   b) modifying the diet to include low tryptamine levels; and/or
   c) consideration of the controlling of the balance between neurodegenerative and anticancer involving the natural effects of tryptamine.

7) The effect of tryptamine is "dose-dependent" and tryptamine can be useful for the elimination of the highly malignant human neuroblastic cells concurrently to the stimulation of neuronal differentiation.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A method of generating cellular models demonstrating Alzheimer's-like characteristics comprising:
   a) selecting a human neuroblast cell line including epithelial cells,
   b) subjecting the neuroblast cell line to a solution of trypsin and thereby washing out the neuroblast cells from the epithelial cells in order to segregate the epithelial cells from neuroblast cells in the neuroblast cell line
   c) cultivating the epithelial cells,
   d) isolating the epithelial cells,
   e) separating out the isolated epithelial cells, and acutely treating the separated portion of the epithelial cells with tryptamine to define a grouping of epithelial cells,
   f) treating the grouping of epithelial cells with generally about 50 to 100 micrograms/milliliters of tryptamine in a culture medium for a period of up to 60 days, and
   g) generating new neurofibrillary tangles and changes of cytoskeleton associated tryptophanyl-tRNA synthetase (TrpRS) within the grouping of epithelial cells.

2. A method as recited as claim 1 wherein the step of isolating the epithelial cells further comprises isolating the epithelial cells to define a grouping characterized by expressing a differentiated neuron-axon phenotype.

3. A method as recited in claim 1 wherein the step of segregating the epithelial cells from the neuroblast cells further comprises the step of treating the neuroblast cell line with generally between 20 to 40 micrograms/milliliters of tryptamine.

4. A method as recited in claim 1 wherein the step of cultivating the segregated epithelial cells further comprises cultivating the segregated epithelial cells for a period of time sufficient to allow the inhibitory effects of tryptamine on the segregated epithelial cells to be exhibited.

5. A method as recited in claim 4 wherein the period of time comprises several months.

6. A method as recited in claim 1 further comprising the step of fixing the grouping of epithelial cells in a PBS buffer solution.

7. A method as recited in claim 6 wherein the PBS buffer solution comprises substantially 4% formaldehyde and substantially 0.25% glutaraldehyde.

8. A method as recited in claim 7 further comprising the step of fixing the isolated epithelial cells in the PBS buffer solution for 30 minutes.

9. A method as recited in claim 1 wherein the culture medium comprises RPMI 1640 and the addition of 10% fetal calf serum and antibiotics.

* * * * *